(12) United States Patent
Kendrick

(10) Patent No.: US 7,641,624 B2
(45) Date of Patent: Jan. 5, 2010

(54) FEMUR TRACTION DEVICE

(75) Inventor: Richard L. Kendrick, Mooresville, NC (US)

(73) Assignee: Kendrick EMS, Inc., Mooresville, NC (US)

( * ) Notice: Subject to any disclaimer, the term of this patent is extended or adjusted under 35 U.S.C. 154(b) by 51 days.

(21) Appl. No.: 11/450,181

(22) Filed: Jun. 9, 2006

(65) Prior Publication Data

US 2007/0287946 A1    Dec. 13, 2007

(51) Int. Cl.
*A61F 5/00* (2006.01)
(52) U.S. Cl. .............................. 602/36; 602/23; 602/32; 602/38
(58) Field of Classification Search ............. 602/32–38, 602/5, 23; 128/878, 882, 846, 870, 877, 128/872, 845; 606/237, 241–244
See application file for complete search history.

(56) References Cited

U.S. PATENT DOCUMENTS

| | | | | |
|---|---|---|---|---|
| 2,198,908 A | | 4/1940 | Ellis | |
| 2,319,609 A | * | 5/1943 | La Crosse | 602/40 |
| 3,419,002 A | * | 12/1968 | Santosus | 602/23 |
| 4,328,794 A | * | 5/1982 | Holmes | 602/5 |
| 4,708,131 A | * | 11/1987 | Kendrick | 602/23 |
| 4,911,152 A | * | 3/1990 | Barnes et al. | 602/23 |
| 5,074,289 A | * | 12/1991 | Leibinsohn | 602/23 |
| 5,342,288 A | * | 8/1994 | Lee et al. | 602/5 |
| 2004/0140152 A1 | * | 7/2004 | Richardson | 182/3 |

* cited by examiner

*Primary Examiner*—Kim M Lewis
(74) *Attorney, Agent, or Firm*—Summa, Additon & Ashe, P.A.

(57) ABSTRACT

A femur traction device includes a brace adapted to be secured to a patient's leg, with one end secured above a break in the leg and a hitch end extending below the foot and providing a hitch for a tensioning harness. The tensioning harness is secured between the hitch and the patient's ankle, and straps of the harness may be lengthened or shortened to increase or decrease tension on the leg. The tensioning harness advantageously does not rely on hook-and-loop type fastening means, is color coded to facilitate proper use, and stores in a pouch that forms part of and is secured to the remainder of the tensioning harness.

6 Claims, 2 Drawing Sheets

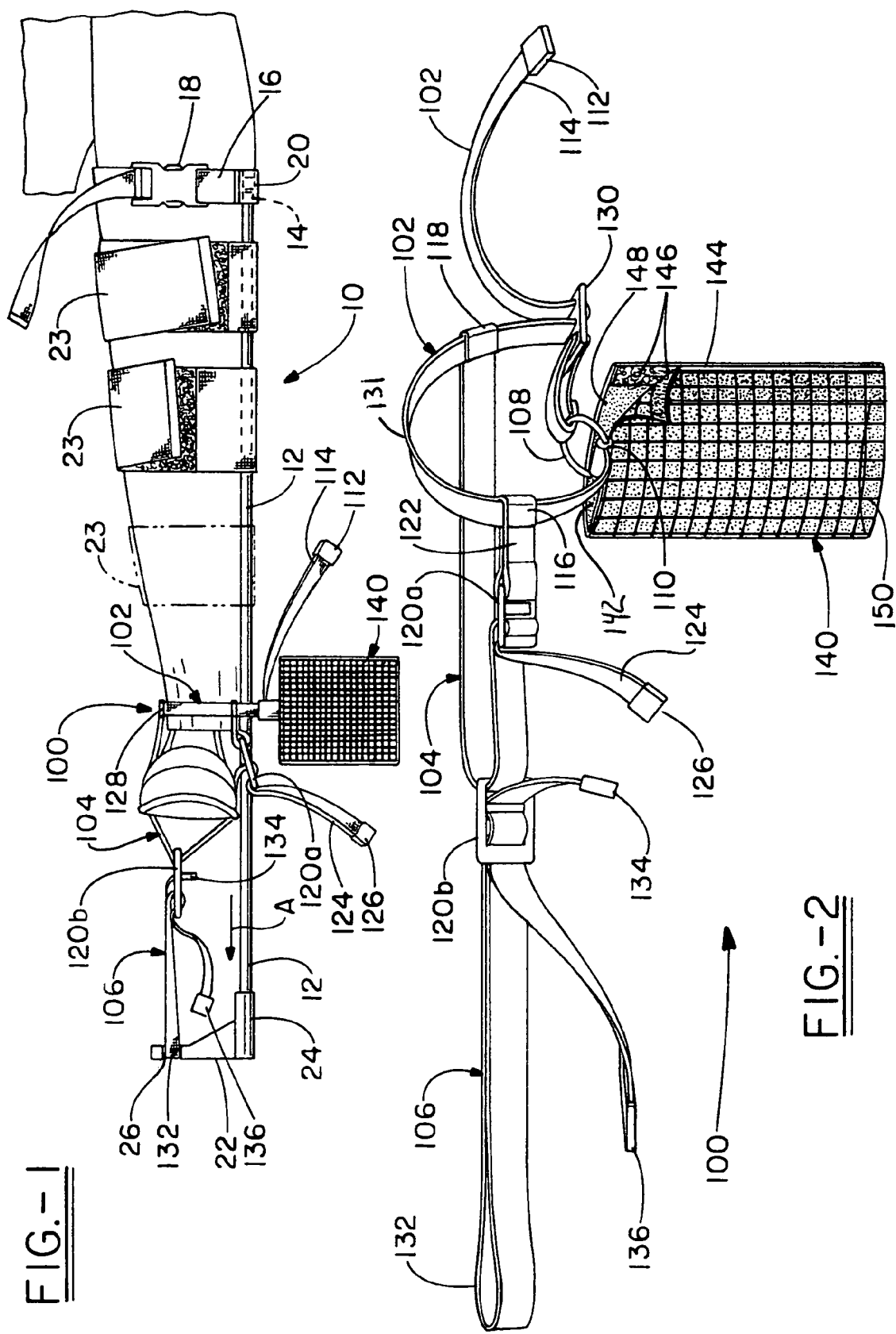

FEMUR TRACTION DEVICE

TECHNICAL FIELD

The invention is in the field of paramedical assistance devices and the provision of emergency aid to a victim suffering from a broken leg, typically a broken femur. In one embodiment, the invention relates to a femur traction device employing a special leg harness to secure an injured individual's leg to the traction device. In another embodiment, the invention relates to a femur traction device employing a tension-adjusting device. In a particularly preferred embodiment, this invention relates to a femur traction device employing a special leg harness and a tension-adjusting device.

BACKGROUND ART

When the femur is broken, the leg muscles will involuntarily contract unless traction is applied to the leg. If left to contract involuntarily for a period of time, the muscles will spasm, leading to fibrillation, in which the muscles spastically vibrate beyond the control of the injured individual. This causes complications in treating the broken femur, especially in the case of a complex fracture in which the broken segments of the femur are misaligned, with jagged, broken portions digging into the flesh. Spasms or fibrillation pose a serious threat to the well-being and life of the victim. Large arteries and other blood vessels passing alongside the femur bone are at risk of being severed, which can cause rapid blood loss and even death, sometimes within as little time as two minutes. For this reason, when a paramedic is at the scene of an accident and the accident victim has a broken femur, the leg is quickly placed in traction using a portable traction device.

One prior art traction device that is widely used by paramedic units is disclosed in U.S. Pat. No. 4,708,131. The device disclosed therein utilizes a single pole or brace, extending along the outside of the injured leg. The brace is secured to the leg, above the break, and extends below the foot to a terminal end where a hitch is provided. A tensioning harness is secured to the ankle and the hitch and has tensioning means for pulling the ankle toward the hitch. This places the injured leg in traction and prevents or at least lessens the aforementioned spasms or fibrillation. The brace may be segmented.

Although this prior art device has been well received by paramedics and other medical professionals, it does have some disadvantages. The tensioning harness is secured to the ankle by a cuff that is adjustable through the overlapping of material straps having hook-and-loop fasteners, and it has been found that such a securing system is less than satisfactory, and even inoperable, in inclement weather. Mist, rain, snow, sand and other debris compromises the ability of the user to establish a good connection between the hooks and the loops.

The cuff portions of the prior art devices, including but not limited to the commercial embodiment of the device of U.S. Pat. No. 4,708,131, are sized too small for some applications. For instance, if a skier breaks a leg and a prior art traction device must be employed to place the leg in traction, the ankle cuff will be too small to fit around the skier's ski boot. This problem also occurs with construction workers and other laborers wearing large boots, and with hunters or hikers. The hook-and-loop wrap provided in the prior art is neither sufficiently large nor sufficiently adjustable for all applications in which the tensioning harness may need to be employed.

It is also common for the prior art tensioning harness to become lost or entangled in other equipment carried by paramedics or other entities that employ femur traction devices. This is due, in part, to human nature and the tendency for packing away the femur traction device components in a speedy manner rather than a particularly organized manner. If lost, the femur traction device becomes nearly useless, and improvisation is necessary to employ it as it should be employed. If tangled in other equipment, time spent untangling it takes away from time spent treating the patient. Thus, means for keeping the harness in good order and keeping it with the remainder of the femur traction device equipment is needed.

It should also be appreciated that, when placing an injured leg in traction, it might be preferable to fine-tune the degree of tensioning. This is very difficult to do simply through the adjustment of straps on a tensioning harness, as is currently practiced. Therefore, this invention also provides a tension-adjusting device that allows for fine adjustments of the tension established by the traction device, without having to rely upon the adjustment of the length of straps in a tensioning harness.

SUMMARY OF THE INSTANT INVENTION

The instant invention is addressed toward the above-stated drawbacks in the prior art and consists of a new tensioning harness for use with traction device elements functioning similarly to those shown in U.S. Pat. No. 4,708,131.

It is an object of this invention to provide a tensioning harness that can be quickly secured around an ankle, without relying on hook-and-loop type fasteners that fail under certain conditions.

It is another object to provide a tensioning harness that can be stored to keep the harness in good order and separated from the elements of other equipment with which it might be employed.

It is yet another object to provide a tension-adjusting device for use with a tensioning harness and traction device. This tension-adjusting device might be employed with tensioning harnesses in accordance with this invention or those of the prior art.

These and other objects of the present invention, as well as the advantages thereof over existing prior art forms, which will become apparent from the description to follow, are accomplished by the improvements hereinafter described and claimed.

In general, this invention provides a femur traction device for use in applying traction to a broken leg. The femur traction device includes a brace having a first end opposite a hitch end, and a thigh strap adapted to engage around the broken leg, at the thigh, and, when placed around the leg in this manner, engages the first end of said brace. A tensioning harness is provided including an ankle strap, a stirrup, a fastener receipt, a fastener, and a tensioning strap. The ankle strap has a first end and a second end, and the stirrup is secured to the ankle strap and adapted for looping around the foot at the end of the broken leg. A first end of the stirrup is secured to the ankle strap between said first and said second ends of said ankle strap, and a second end of the stirrup is secured to the ankle strap between said first end of the stirrup and the second end of the ankle strap. The fastener receipt is secured to said ankle strap and the fastener is movable along said ankle strap and capable of being selectively secured to the fastener receipt to loop a portion of said ankle strap around the ankle of the broken leg. The tensioning strap is selectively secured to the hitch end of said brace and is secured to the stirrup by tensioning buckle.

In accordance with another embodiment, this invention provides a femur traction device that employs a tension-adjusting device. The femur traction device includes a brace having a first end opposite a hitch end, and a thigh strap adapted to engage around a broken leg at the thigh and to engage the first end of the brace. A harness is provided for securing around the foot of the broken leg. The tension-adjusting device includes a hitch body that is secured to the hitch end of the brace and extends therefrom to provide a threaded bore. A threaded tensioning shaft is threaded through the threaded bore and provides a knob at one end thereof and a harness received at the opposite end thereof. The harness receives a portion of the harness such that the harness is moved by the turning of the knob, which causes the advancement of the threaded tensioning shaft through the threaded bore. In particular embodiments, the hitch body may be secured to the base through a brace sleeve, and may carry a tension indicator and tension gauge.

In yet another embodiment of this invention is provided a femur traction device for use in applying traction to a broken leg comprising a brace having a first end opposite a hitch end; a thigh strap adapted to engage around the leg at the thigh and to engage said first end of said brace; a tensioning harness including an ankle strap having a first end and a second end, a stirrup secured to said ankle strap and adapted for looping around the foot at the end of the broken leg, said stirrup having a first end secured to said ankle strap between said first end and said second end of said ankle strap and a second end secured to said ankle strap between said first end of said stirrup and said second end of said ankle strap, a fastener receipt secured to said ankle strap, a fastener movable along said ankle strap and selectively secured to said fastener receipt to loop a portion of said ankle strap around the ankle of the broken leg, and a tensioning strap secured to said stirrup by a tensioning buckle. The device further comprises a tension-adjusting device including a hitch body secured to said hitch end of said brace and extending therefrom to provide a threaded bore, and a threaded tensioning shaft threaded through said threaded bore and providing a knob at one end thereof and a harness receipt at the opposite end thereof, said harness receipt receiving a portion of said tensioning strap such that said tensioning strap is moved by the turning of said knob, which causes the advancement of said threaded tensioning shaft through said threaded bore.

A preferred exemplary femur traction device according to the concepts of the present invention is shown by way of example in the accompanying drawings without attempting to show all the various forms and modifications in which the invention might be embodied, the invention being measured by the appended claims and not by the details of the specification.

BRIEF DESCRIPTION OF THE DRAWINGS

FIG. 1 is a top view illustrating the use of a combination traction device and tensioning harness in accordance with this invention.

FIG. 2 shows a particularly preferred tensioning harness for use with a traction device.

PREFERRED EMBODIMENT FOR CARRYING OUT THE INVENTION

Figure 3:
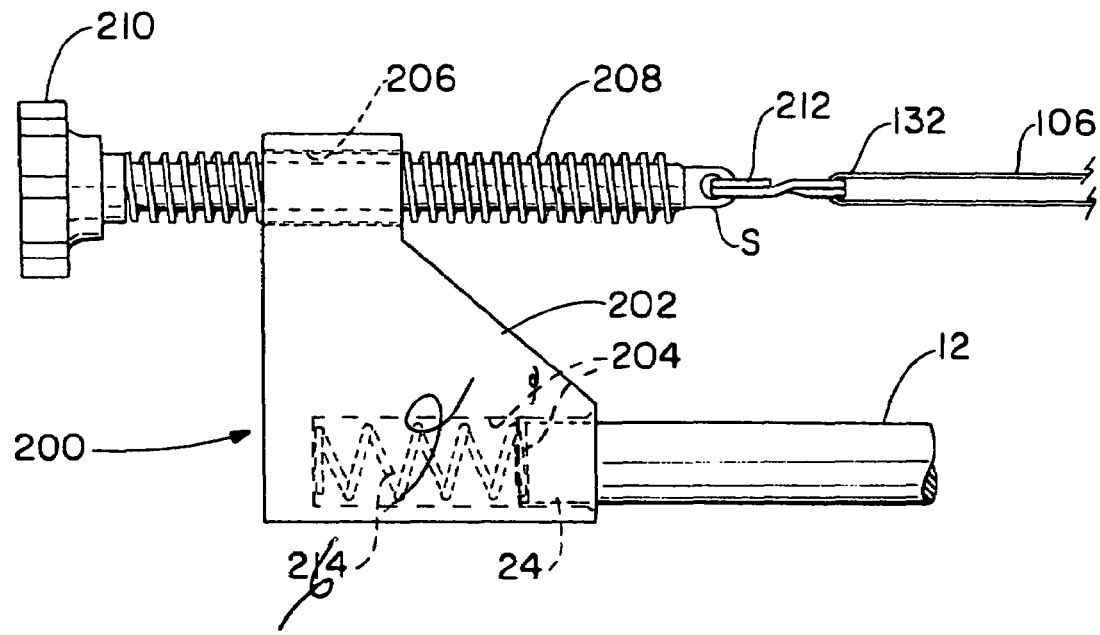
FIG. 3 shows one embodiment of a tension-adjusting device of this invention.

Referring now to FIG. 1, a particularly preferred traction device in accordance with this invention is shown and designated by the numeral 10. Traction device 10 includes brace 12, which may be segmented as taught in prior U.S. Pat. No. 4,708,131 (with appropriate structure changes being made to the thigh strap). Thigh end 14 of brace 12 is engaged by thigh strap 16, which is wrapped around the injured individual's upper thigh and secured to thigh end 14, preferably above the break in the leg. Thigh strap 16 is preferably adjustable through quick-release, quick-tightening buckle 18, which, in the FIGS. is shown as a well known buckle having mating male and female members. Brace 12 is secured to thigh strap 16 at socket 20, which is closed to further movement of brace 12 to the right in FIG. 1. The socket is symmetrical, so that either side could be used. This is a very useful feature, because in the field, when such emergency devices are generally being used, it is typically dark, the weather may be bad, and confusion rules. By making the socket double-ended, it makes no difference whether the operator gets it on right side up or upside down. Brace 12 is designed to extend a few inches below the bottom of the foot, to hitch end 24, where hitch 22 is provided. Through the use of a tensioning harness, the ankle is pulled toward hitch 22 to place the leg in traction.

A tensioning harness in accordance with this invention is shown in FIG. 2 and designated by the numeral 100. Tensioning harness 100 is secured to an individual at the ankle area and secured to brace 12 at hitch 22 so that the individual's leg can be pulled toward hitch 22 and placed under tension. More particularly, ankle strap 102 is secured around the injured individual's ankle, with stirrup 104 extending to loop around the foot, and tensioning strap 106, which is secured between hitch 22 and stirrup 104, is shortened to pull stirrup 104 and thus the ankle toward hitch 22, in the direction of arrow A. Harness 100 is used after brace 12 is secured to the patient with hitch 22 below the foot.

In FIG. 2, it can be seen that ankle strap 102 extends from fastener receipt 108 at first end 110 to stop 112 at second and 114. Stirrup 104 is connected to ankle strap 102 at both first end 116 and second end 118. Tensioning buckle 120a is secured proximate first end 116 by a length of strap 122, and stirrup strap 124 extends from ankle strap 102 at second end 118 of stirrup 104 to communicate with tensioning buckle 120a to complete stirrup 104. More particularly, stirrup strap 124 extends through tensioning buckle 120a to stop 126, and the length extending beyond buckle 120a is either pulled to shorten stirrup 104 or is fed back through buckle 120a to lengthen stirrup 104. Tensioning buckle 120a is of the well-known type wherein, once a length of strap is feed therethrough or pulled therethrough, the length of strap extending beyond the buckle is maintained. Typically, the buckle itself must be manipulated to place slots therein in a particular position with respect to the strap to permit the strap to flow through the buckle. Stop 126 prevents stirrup strap 124 from being completely pulled through buckle 120a during a lengthening of stirrup 104.

As can be seen in FIG. 1, stirrup 104 is typically not drawn tightly across the bottom of the patent's foot, but rather is pulled by tensioning strap 106,to pull the ankle cuff 128 formed by securing ankle strap 102 around the patient's ankle, by securing moveable fastener 130 to fastener receipt 108 and pulling any excess length in ankle strap 102 through moveable fastener 130. Moveable fastener 130, as its name implies, is moveable along the length of ankle strap 102, from second end 118 of stirrup 104 to stop 112. Moveable fastener 130 is similar to tensioning buckle 120 in that it maintains its position on ankle strap 102 unless it is manipulated to reside at a different position. That is, moveable fastener 130 is not easily moved along the length of ankle strap 102, and can maintain its position even if force is applied to ankle strap 102 to try and pull it through moveable fastener 130. It can be seen that moveable fastener 130 has a hook end 133 to secure it to fastener receipt 108. Other fastening means could be employed in accordance with the general teaching herein.

To help locate stirrup 104 appropriately, with stirrup 104 running down one side of the patient's foot and up the opposite side, shin piece 131, defined between first and second ends 116 and 118 of ankle strap 102 is preferably placed against the front of the shin, moveable fastener 130 is passed behind the leg and over brace 12 and connected to fastener receipt 108. Excess length of ankle strap 102 is then pulled through moveable fastener 130 to cinch ankle strap 102 tightly around the patient's ankle or boot, etc., and to keep the bottom of the leg associated with brace 12. A plurality of auxiliary straps 23 may be employed at various positions along the patient's leg to further secure it to brace 12. Thereafter, the size of stirrup 104 may be adjusted as desired by manipulating stirrup strap 124 as already disclosed.

Once stirrup strap 104 is secured around the foot by the formation of ankle cuff 128, hitch loop 132 of tensioning strap 106 is slipped over hitch 22 at hitch end 24 of brace 12. Hitch 22 is shaped with loop notch 26, as shown in FIG. 1, so that, once hitch loop 132 is slipped over it, it will remain securely in place. With tensioning strap 106 in place, it is pulled at stop end 136 to shorten the length of tensioning strap 106 between hitch 22 and stirrup strap 104, thus placing the patient's leg under tension between thigh strap 16 and hitch 22. In the embodiment shown, tensioning strap 106 extends through tensioning buckle 120b, with stop end 136 engaging tensioning buckle 120b and incapable of being pulled therethrough. From stop end 136, tensioning strap 106 extends through tensioning buckle 120b and folds back on itself to create hitch loop 132. From there it feeds again through tensioning buckle 120b and terminates at stop end 136. As with tensioning buckle 120a, tensioning buckle 120b tends to maintain the length of tensioning strap 106 fed therethrough, absent manipulation of tensioning buckle 130b to lie in a particular orientation with respect to the length of strap 106 extending therethrough to stop end 136. Stirrup 104 may also be adjusted to increase or decrease the tension.

Because of the conditions that usually prevail at accident sites, it is highly desirable that the straps be color coded to assist the operator in correctly sequencing the steps of attachment despite distractions that might frustrate the operator's ability to concentrate. As mentioned, after brace 12 is in place, tensioning harness 100 is put in place by securing ankle strap 102 around the patient's ankle and then securing harness 100 to brace 12 at hitch 22, through the interaction of hitch loop 132 and hitch 22. Then, stirrup 104 is appropriately adjusted for the patient's foot size by pulling on stop end 126. Finally, stop end 136 of tensioning strap 106 is pulled to put the patient's leg under tension. Thus, in accordance with a preferred embodiment, ankle strap 102 and hitch loop 132 are preferably red, stop end 126 of stirrup strap 104 is preferably yellow, and stop end 136 of tensioning strap 106 is preferably green, so that these securement and tightening steps can be performed by following a green-yellow-red step sequence that will be easy to remember and guide the operator under stressful conditions so that the attachment will go smoothly.

Tensioning harness 100 preferably includes an attached pouch 140 in which the remainder of tensioning harness 100 may be stored. In the preferred embodiment shown, pouch 140 is secured to first end 110 of ankle strap 102 at an open end 142 of pouch 140 such that the remainder of harness 100 can easily be stuffed into open end 142. Pouch 140 also preferably opens along side 144, which connects with open end 142 such that pouch 140 can be manipulated to open up widely for the acceptance of the remainder of harness 100. Side 144 is preferably selectively opened and closed by hook-and-loop type fasteners as represented at 146. Other fasteners may be employed. At least one face 148 or 150 of pouch 140 (here it is 150) is made of a mesh type material in order to reduce weight, aid in drying of the harness, when necessary, and to provide visual access to the interior to help one identify that the leg harness is retained therein.

With these advantages, in addition to the major advantage of being much faster to use than existing units, and costing only a fraction as much, the unit is a real contribution to emergency and paramedical equipment.

Although this invention is not necessarily limited to or by any particular dimensions, the following are provided for guidance in constructing the leg harness in accordance with particularly preferred embodiments of this invention. Ankle strap 102 is, in one embodiment, from 24 to 36 inches long, in another, from 30 to 32 inches long, from first end 110 to second end 114. The distance between first end 116 and second end 113 of stirrup strap 104 in long ankle strap 102, is, in one embodiment, from 4 to 8 inches, in another, from 4.5 to 5 inches. The length of stirrup 104, from first end 116 to second end 118, can range from 20 inches, when fully lengthened, to 6 inches, when fully shortened. Tensioning strap 106 is preferably 20 inches in length from hitch loop 132 to stop 134. To retain such a leg harness, pouch 140 is preferably rectangular, having a length of from 7 to 8 inches, and a width of from 4 to 5 inches.

Referring now to FIG. 3, an embodiment of a tension-adjusting device that can be employed with either the tensioning harness disclosed hereinabove or with any other prior art harness, as shown and designated by the numeral 200. Tension-adjusting device 200 includes hitch body 202 which, much like hitch 22 disclosed with respect to the tensioning harness hereinabove, fits on hitch end 24 of a brace 12. Hitch body 202 includes a brace sleeve 204 that sits on hitch end 24, as shown. This fit can be permanent or removable. In an embodiment that will be shown hereinbelow, this engagement can be configured with other elements to provide means for visually reading the tension established by a femur traction device.

Hitch body 202 extends outwardly from brace 12 to extend below the foot of a patient when brace 12 is secured along a patient's leg, for example, as shown in FIG. 1, but, rather than providing loop notch 26, provides a threaded bore, as at 206. Threaded bore 206 receives threaded tensioning shaft 208 having knob 210 at the end distance from the patient's foot and harness receipt 212 at the end more proximate the patient's foot. Harness receipt 212 can receive hitch loop 132 of tensioning harness 100 or otherwise receive a portion of a differently configured harness. Upon securing the harness to harness receipt 212, tension to the leg can he increased by rotating knob 210 that advances tensioning shaft 208 to the left, away from the patient's foot. Similarly, tension can be decreased by rotating knob 210 in a direction that advances tensioning shaft to the right, toward the foot. Preferably, a swivel coupling is employed between harness receipt 212 and threaded tensioning shaft 208, as at swivel S.

Figure 4:
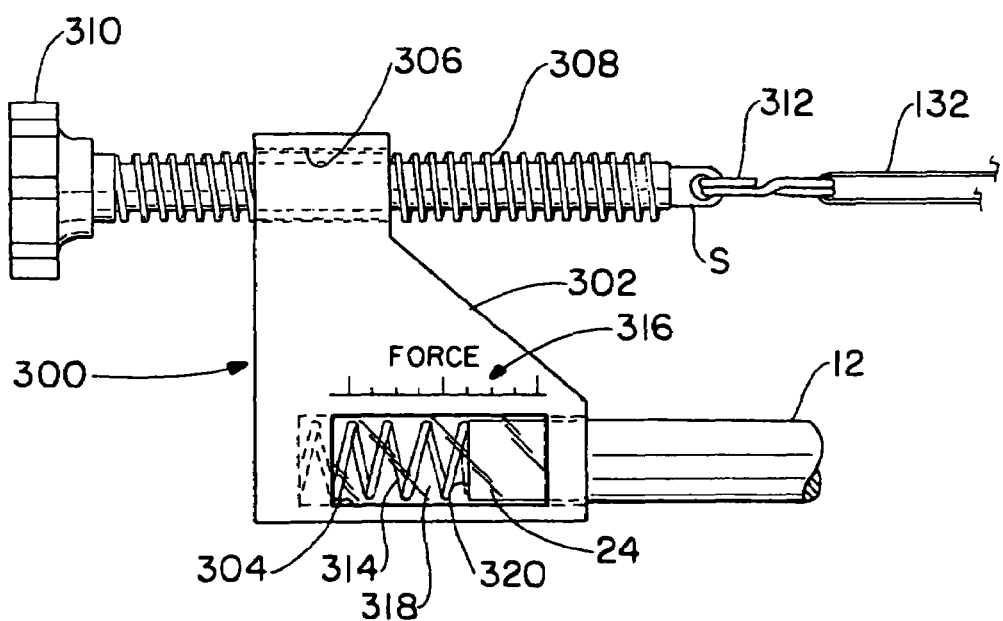
FIG. 4 shows another embodiment of a tension-adjusting device in accordance with this invention.

In an alternative embodiment of a tension-adjusting device as shown in FIG. 4, it is possible to read the tension that has been established by the femur traction device. In FIG. 4, tension-adjusting device 300 is similar to tension-adjusting device 200, with like parts receiving like numerals although increased by 100. Thus, tension-adjusting device 300 includes hitch body 302, which engages hitch end 24 of brace 12 at brace sleeve 304. Tension-adjusting device 300 also includes threaded bore 306, which receives threaded tensioning shaft 308 providing knob 310 and harness receipt 312. The distinction between tension-adjusting device 200 and the present tension-adjusting device 300, is that spring member 314 is disposed in brace sleeve 304 to push on brace 12 in a direction forcing brace 12 out of brace sleeve 304. Spring member 314 is, however, preferably not long enough to actually force brace 12 fully out of brace sleeve 304. Tension gauge 316 is provided on hitch body 302 to be viewed thereon, and brace sleeve window 318 permits the viewing of terminal end 320 of brace 12, such that the position of terminal end 320 can provide a reading from tension gauge 316. It will be appreciated that by adjusting the tension through the adjustment of tension-adjusting device 300 through knob 310, different tensions can be achieved and will be able to be read at tension gauge 316.

In light of the foregoing, it should thus be evident that a femur traction device constructed as described herein substantially improves the art and otherwise accomplishes the objects of the present invention.

What is claimed is:

1. A femur traction device for use in applying traction to a broken leg comprising:
    a brace having a first end opposite a hitch end;
    a thigh strap adapted to engage around the leg at the thigh and to engage said first end of said brace;
    a harness for securing around the foot of the broken leg, said harness having a tensioning strap attached thereto; and
    a tension-adjusting device including:
        a hitch body secured to said hitch end of said brace and extending therefrom to provide a threaded bore; and
        a threaded tensioning shaft threaded through said threaded bore and providing a knob at one end thereof and a harness receipt at the opposite end thereof, said harness receipt attached to said tensioning strap of said harness, said threaded tensioning shaft extending substantially parallel with respect to said brace, said harness receipt receiving said tensioning strap such that said harness is moved by the turning of said knob, which causes the advancement of said threaded tensioning shaft through said threaded bore;
        wherein said threaded tensioning shaft and said tensioning strap move along substantially the same axis in a substantially longitudinal direction with respect to said brace.

2. A femur traction device for use in applying traction to a broken leg comprising:
    a brace having a first end opposite a hitch end;
    a thigh strap adapted to engage around the leg at the thigh and to engage said first end of said brace;
    a harness for securing around the foot of the broken leg; and
    a tension-adjusting device including:
        a hitch body secured to said hitch end of said brace and extending therefrom to provide a threaded bore;
        a threaded tensioning shaft threaded through said threaded bore and providing a knob at one end thereof and a harness receipt at the opposite end thereof, said harness receipt receiving a portion of said harness such that said harness is moved by the turning of said knob, which causes the advancement of said threaded tensioning shaft through said threaded bore, wherein said hitch body is secured to said brace through a brace sleeve in said hitch body that receives said hitch end of said brace.

3. The femur traction device of claim 2, further comprising a spring member disposed in said brace sleeve to push on said brace in a direction out of said brace sleeve.

4. The femur traction device of claim 3, further comprising a tension gauge readable on said hitch body.

5. The femur traction device of claim 4, further comprising a brace sleeve window that permits viewing of a terminal end of said brace such that the position of said terminal end can provide a reading from said tension gauge.

6. A femur traction device for use in applying traction to a broken leg comprising:
    a brace having a first end opposite a hitch end;
    a thigh strap adapted to engage around the leg at the thigh and to engage said first end of said brace;
    a tensioning harness including:
        an ankle strap having a first end and a second end,
        a stirrup secured to said ankle strap and adapted for looping around the foot at the end of the broken leg, said stirrup having a first end secured to said ankle strap between said first end and said second end of said ankle strap and a second end secured to said ankle strap between said first end of said stirrup and said second end of said ankle strap,
        a fastener receipt secured to said ankle strap,
        a fastener movable along said ankle strap and selectively secured to said fastener receipt to loop a portion of said ankle strap around the ankle of the broken leg, and
        a tensioning strap secured to said stirrup by a tensioning buckle; and
    a tension-adjusting device including:
        a hitch body secured to said hitch end of said brace and extending therefrom to provide a threaded bore;
        a threaded tensioning shaft threaded through said threaded bore and providing a knob at one end thereof and a harness receipt at the opposite end thereof, said harness receipt receiving a portion of said tensioning strap such that said tensioning strap is moved by the turning of said knob, which causes the advancement of said threaded tensioning shaft through said threaded bore, wherein said hitch body is secured to said brace through a brace sleeve in said hitch body that receives said hitch end of said brace.

* * * * *